United States Patent
Boateng et al.

(10) Patent No.: US 9,199,222 B2
(45) Date of Patent: Dec. 1, 2015

(54) REMOVAL OF LIGHT FLUOROALKANES FROM HYDROCARBON STREAMS

(71) Applicants: Kenneth A. Boateng, Brights Grove (CA); Marc-Andre Poirier, Sarnia (CA)

(72) Inventors: Kenneth A. Boateng, Brights Grove (CA); Marc-Andre Poirier, Sarnia (CA)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 212 days.

(21) Appl. No.: 13/905,303

(22) Filed: May 30, 2013

(65) Prior Publication Data
US 2013/0259770 A1 Oct. 3, 2013

Related U.S. Application Data

(62) Division of application No. 12/961,711, filed on Dec. 7, 2010, now Pat. No. 8,487,155.

(51) Int. Cl.

| | |
|---|---|
| *B01J 38/48* | (2006.01) |
| *B01J 38/52* | (2006.01) |
| *B01J 27/02* | (2006.01) |
| *C07C 7/12* | (2006.01) |
| *B01J 39/04* | (2006.01) |
| *B01J 39/08* | (2006.01) |
| *B01J 39/10* | (2006.01) |
| *B01J 39/14* | (2006.01) |
| *B01J 39/18* | (2006.01) |
| *B01J 49/00* | (2006.01) |
| *B01J 27/053* | (2006.01) |
| *B01J 31/10* | (2006.01) |

(52) U.S. Cl.
CPC ............ *B01J 27/02* (2013.01); *B01J 27/053* (2013.01); *B01J 31/10* (2013.01); *B01J 39/043* (2013.01); *B01J 39/085* (2013.01); *B01J 39/10* (2013.01); *B01J 39/14* (2013.01); *B01J 39/185* (2013.01); *B01J 49/0008* (2013.01); *B01J 49/0078* (2013.01); *C07C 7/12* (2013.01); *B01J 2219/00006* (2013.01); *B01J 2220/603* (2013.01)

(58) Field of Classification Search
None
See application file for complete search history.

(56) References Cited

U.S. PATENT DOCUMENTS

| | | | |
|---|---|---|---|
| 2,347,945 | A | 5/1944 | Frey et al. |
| 2,403,714 | A | 7/1946 | Frey |
| 2,461,523 | A | 2/1949 | Donald et al. |
| 3,624,166 | A | 11/1971 | Fuhrmann et al. |
| 3,966,417 | A | 6/1976 | Chapman |
| 4,317,949 | A | 3/1982 | Vaughan |
| 4,820,884 | A | 4/1989 | Weigert |
| 5,223,464 | A * | 6/1993 | Michaelson et al. ............ 502/33 |
| 5,322,673 | A | 6/1994 | Eason |

(Continued)

OTHER PUBLICATIONS

Greally et al., "Retention Behaviour of Volatile C1-C3 Fluoroalkanes Upon Selected Preconcentration Adsorbents", Journal of Chromatography A, vol. 1133, pp. 49-57 (2006).

(Continued)

*Primary Examiner* — Tam M Nguyen
(74) *Attorney, Agent, or Firm* — Glenn T. Barrett; Andrew T. Ward

(57) ABSTRACT

The removal of fluoroalkanes from fluoroalkane-containing hydrocarbon streams, preferably $C_3$ to $C_5$ hydrocarbon streams. The fluoroalkane-containing hydrocarbon stream is contacted with an adsorbent containing a strong acid function, preferably a silica gel or a strong cation ion-exchange resin having sulfonic acid functionality.

10 Claims, 2 Drawing Sheets

(56) References Cited

U.S. PATENT DOCUMENTS

| | | |
|---|---|---|
| 5,396,022 A | 3/1995 | Wu et al. |
| 7,074,434 B2 | 7/2006 | Lambert et al. |
| 7,446,238 B2 | 11/2008 | Hovis et al. |
| 7,750,195 B2 | 7/2010 | Wilmet et al. |
| 8,093,441 B2 | 1/2012 | Poirier et al. |
| 2010/0160706 A1 | 6/2010 | Poirier et al. |

OTHER PUBLICATIONS

Chandra et al "Alkylation of Phenol With MTBE and Other TERT-BUTYL Ethers: Cation Exchange Resins As Catalysts", Catalysis Letters 19, pp. 309-317 (1993).

Tanabe et al., "Industrial Application of Solid Acid-Base Catalysts", Applied Catalysis A: General 181, pp. 399-434 (1999).

\* cited by examiner

REMOVAL OF LIGHT FLUOROALKANES FROM HYDROCARBON STREAMS

FIELD

The present invention relates to the removal of fluoroalkanes from fluoroalkane-containing hydrocarbon streams, preferably $C_3$ to $C_{10}$ hydrocarbon streams. The fluoroalkane-containing hydrocarbon stream is contacted with an adsorbent containing a strong acid function, preferably a silica gel having sulfonic acid functionality or a strong cation ion-exchange resin having sulfonic acid functionality.

BACKGROUND

Certain processes for upgrading hydrocarbon feeds using fluorine-containing catalysts generate organic fluorine-containing by-products. These processes may involve reactions such as polymerization and alkylation of relatively low boiling hydrocarbons to produce octane enhancers. The fluorine-containing by-products, which are typically fluoroalkanes, are undesirable because they can decompose at elevated temperatures, for example during fractional distillation or combustion, to form hydrofluoric acid (HF) which is corrosive and toxic. One process of particular interest is the HF alkylation of relatively low-boiling hydrocarbons using hydrofluoric acid to produce higher boiling hydrocarbons used as octane enhancers. Although the precise compositions of the fluoroalkanes are difficult to establish, it is believed they are predominately $C_4$ fluoroalkanes, more particularly 2-fluoro-2-methylpropane (tert-butyl fluoride). The presence of these light fluoroalkanes in n-butane and other hydrocarbon streams is undesirable and may limit the applicability of the hydrocarbon product for some purposes, or result in lower market value.

Various attempts have been made to remove undesirable fluoroalkanes from hydrocarbon streams. For example, U.S. Pat. No. 5,396,022, which is incorporated herein by reference, relates to the defluorination of alkane streams comprising treating an alkane/fluoroalkane stream with an acidic alumina, preferably a sulfur-containing alumina, to reduce the amount of fluoroalkanes in the feed.

Also, U.S. Pat. Nos. 2,347,945 and 2,403,714, both of which are incorporated herein by reference, relate to the removal of organic fluorine compounds from a hydrocarbon stream by contacting the hydrocarbon stream with porous materials, such as alumina gel, activated alumina, dehydrated bauxite, chromium oxide, a mixture of alumina and chromium oxide, metals of the iron group, and the like.

While commercially viable processes exist for removing fluoroalkanes from light hydrocarbon streams, there nevertheless remains a need in the art for ever more efficient and cost effective processes for removing these fluoroalkanes.

SUMMARY

According to another aspect of the presently disclosed subject matter, there is provided a process for removing fluoroalkanes from hydrocarbon streams comprised of $C_3$ to $C_{10}$ hydrocarbons and containing from about 0.01 to about 1 wt. % $C_3$ to $C_5$ fluoroalkanes, or from about 0.01 to about 3 wt. % $C_3$ to $C_5$ fluoroalkanes, wherein the process comprises contacting the fluoroalkane-containing hydrocarbon stream with an adsorbent having strong acid functionality, which contacting is performed at a temperature from about −40° C. to about 60° C. In one embodiment, the fluoroalkane-containing hydrocarbon stream includes from about 1 to about 3 wt. % $C_3$ to $C_5$ fluoroalkanes. The adsorbent can be housed in at least two reactors, and the fluoroalkane-containing hydrocarbon stream is introduced to the at least two reactors in series. The adsorbent can be any one of the absorbents described herein.

In a preferred embodiment the fluoroalkane-containing hydrocarbon stream is comprised of at least 75 wt. % $C_3$ to $C_5$ hydrocarbons.

In another preferred embodiment the acid functionality of the adsorbent is sulfonic acid.

In still another preferred embodiment the adsorbent is a silica gel or an ion-exchange resin containing a sulfonic acid functionality.

In yet another preferred embodiment the fluoroalkanes to be removed are characterized as having from about 3 to 5 carbon atoms and 1 or 2 fluorine atoms.

In other preferred embodiments the fluoroalkanes to be removed are selected from the group consisting of 1-fluoropropane, 2-fluoropropane, 2-fluoro-2-methylpropane, 1-fluorobutane, 2-fluorobutane, 1-fluoro-2-methylbutane, 1-fluoropentane, 2-fluoropentane, 2,2-difluorobutane, 3-fluoropentane, 1,2-difluoropentane, 1-fluoro-3-methylbutane, and mixtures thereof.

In accordance with another aspect of the present invention there is provided a process for removing fluoroalkanes from hydrocarbon streams comprised of $C_3$ to $C_{10}$ hydrocarbons and containing from about 0.05 to about 1 wt. % $C_3$ to $C_5$ fluoroalkanes, wherein the process comprises contacting the fluoroalkane-containing hydrocarbon stream with an adsorbent having strong acid functionality, which contacting is performed at a temperature from about −40° C. to about 60° C.

According to an alternative aspect of the present application, a process for conditioning a catalyst is provided. In one embodiment, the process includes providing the adsorbent for conditioning, optionally, applying water to the adsorbent, applying an alcohol to the adsorbent, and drying the adsorbent at an elevated temperature. In one embodiment, the catalyst is a strong acid adsorbent, such as any one of the adsorbents described herein. The alcohol can be an isopropyl alcohol, and/or the adsorbent can be dried at a temperature of from about 20° C. to about 80° C. The conditioned catalyst can be provided for use in a process for removing fluoroalkanes from hydrocarbon streams, as described herein.

DETAILED DESCRIPTION

Figure 1:
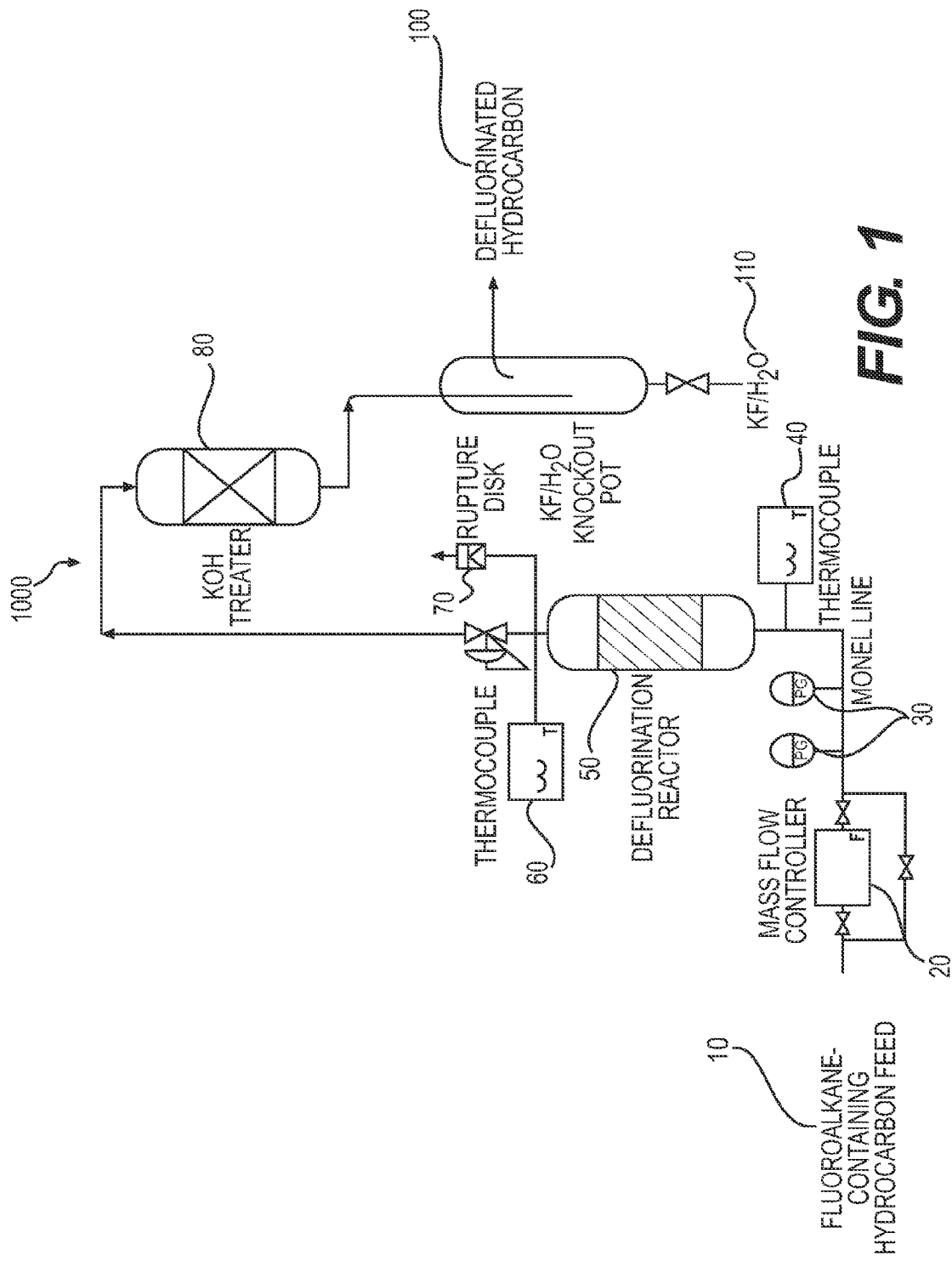
FIG. 1 is a schematic representation of a fluoroalkane removal system suitable for fluoroalkane-containing hydrocarbon feeds in accordance with the process disclosed herein.

Hydrocarbon streams on which the present invention can be practiced are those relatively low boiling streams containing from about 0.05 to about 1 wt. %, preferably from about 0.1 to about 0.5 wt. % fluoroalkanes based on the total weight of the hydrocarbon stream. These hydrocarbon streams are typically referred to as $C_3$ to $C_{10}$. That is, these fluoroalkane-containing hydrocarbon streams are predominantly comprised of hydrocarbons having from about 3 to about 10. In preferred embodiments of the present invention fluoroalkane-containing hydrocarbon stream contains at least 75 wt % $C_3$ to $C_5$ hydrocarbons, and even more preferably at least 90 wt %

$C_3$ to $C_5$ hydrocarbons, based on the dry weight (water-free) of the fluoroalkane-containing hydrocarbon stream.

The fluoroalkanes targeted for removal by the present invention are typically present in low-boiling point hydrocarbon streams such as propane, n-butane, isobutane, pentane, isopentane, hexane, isohexane, heptane, isoheptane (dimethylpentane), octane, isooctane (dimethylhexane and trimethylpentane), nonane, and isononane (trimethylhexane) produced from an alkylation process. Fluoroalkanes can also be present in hydrocarbon streams from depropanization or debutanization processes. The predominant fluoroalkane-containing hydrocarbon stream is typically a hydrocarbon stream containing $C_3$ to $C_{10}$ hydrocarbons that results from an hydrofluoric (HF) alkylation process wherein an isoparaffin, such as isobutane, is reacted with one or more olefins, such as butylene, to produce a higher molecular weight branched chain paraffin (i.e., "alkylate"). Branched chain paraffins are commercially important for increasing the octane of the gasoline pool and for their sensitivity to octane-enhancing additives. The HF alkylation process is typically conducted at temperatures below 100° F. and at an effective pressure to maintain a liquid phase in the alkylation reaction zone. This effective pressure will typically be around 200 psig, preferably 150-160 psig.

The resulting stream from HF alkylation is typically treated over a potassium hydroxide bed to remove water and at least a fraction of preferably substantially all of, residual hydrofluoric acid. However, a significant problem existing in the industry, is that this treatment does not remove fluoroalkane impurities. As disclosed herein, these fluoroalkane impurities are removed from such light hydrocarbon product streams. It is not uncommon for petroleum refineries to produce n-butane streams containing up to about 0.6 wt % fluoride ions that, because of the high fluoride content, must be sold at a reduced market price.

It has unexpectedly been found by the inventors of the present invention hereof that contacting a $C_3$ to $C_{10}$, preferably $C_3$ to $C_5$ paraffinic stream containing a low level, such as about 0.46 wt % of an alkyl fluoride, such as tert-butyl fluoride, with a small amount of adsorbent of the present invention, such as silica gel having sulfonic acid functionality, at an effective temperature, will remove substantially all of the tert-butyl fluoride. The silica gel is preferably functionalized with sulfonic acid groups by treating or reacting the silica gel with chlorosulfonic acid. Commercial alumina adsorbents designed to remove alkyl fluorides and HF from hydrocarbons streams using a "sulfur containing alumina" as taught in U.S. Pat. No. 5,396,022 do not significantly remove tert-butyl fluoride under the same testing conditions.

As disclosed herein, the method for removing fluoroalkane contaminants from the hydrocarbon stream comprises contacting the fluoroalkane-containing hydrocarbon feed stream with an effective amount of an adsorbent having strong acid functionality at a temperature in the range from −40° C. to 60° C. to remove at least about 90 wt % of the fluoroalkanes, preferably to remove more than about 95 wt % of the fluoroalkanes, based on the dry weight of the hydrocarbon feed. Removal of fluoroalkane contaminants can be further increased by conditioning the adsorbent, as described below in greater detail, and/or by housing the adsorbent in at least two reactors, and introducing the fluoroalkane-containing hydrocarbon stream to at least two reactors in series.

Any suitable adsorbent containing strong acid groups, preferably sulfonic acid groups can be used in the practice of the present invention. Both mineral based materials having Si atoms to which the acid group can bond, and organic based materials, preferably polymeric materials having carbon atoms to which the strong acid group can bond, can be used in the practice of the present invention. Non-limiting examples of suitable mineral materials include silica gels and both naturally occurring and synthetic zeolites and clays. The preferred mineral materials for the present invention are the silica gels. Non-limiting examples of suitable organic materials include strong cation exchange resins, preferably the styrene:divinyl benzene copolymers functionalized with sulfonic acid groups. Styrene:divinyl benzene copolymer strong cation exchange resins are commercially available from various vendors, such as the resins marketed under the tradenames D5174DR from Purolite® and Amberlyst® from Rohm and Hass or from Sigma-Aldrich. The ion-exchange resins used in the practice of the present invention can be used in either the gellular or macroreticular spherical bead form.

As previously mentioned, the fluoroalkanes that can be present as impurities in the hydrocarbon (alkane)/fluoroalkane feed stream of the present invention will typically be fluoroalkanes containing about 3 to 5 carbon atoms and one or two fluorine atoms. Non-limiting examples of such fluoroalkanes include 1-fluoropropane, 2-fluoropropane, 2-fluoro-2-methylpropane, 1-fluorobutane, 2-fluorobutane, 1-fluoro-2-methylbutane, 1-fluoropentane, 2-fluoropentane, 2,2-difluorobutane, 3-fluoropentane, 1,2-difluoropentane, 1-fluoro-3-methylbutane and a mixture thereof. The fluoroalkanes targeted by the processes of the present invention are preferably the monofluoroalkanes, more preferably 2-fluoro-2-methylpropane.

The reaction of the fluoroalkane on the catalyst resin results in the defluorination of the fluoroalkane to form a hydrocarbon, possibly an alkene, and hydrogen fluoride. Preferably, the hydrocarbon product obtained with this invention contains less than 1 wppm of fluoroalkanes and negligible amount of hydrogen fluoride after further treatment through a KOH bed or other suitable absorbent for HF. As a non-limiting example, 2-fluoro-2-methylpropane or tert-butyl fluoride reacts on the strong-acid catalyst resin to form isobutylene and HF as illustrated by equation (1).

Equation (1)

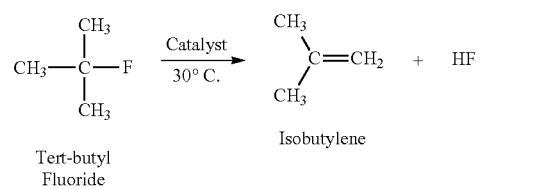

Tert-butyl Fluoride

Isobutylene

The contacting of the hydrocarbon/fluoroalkane feed with the functionalized adsorbent of the present invention can be carried out in any suitable manner including either a batch process or a continuous fixed bed process. A continuous fixed bed process is preferred. The instant process can be carried out at temperatures in the range from about −40° C. to about 60° C., preferably from about −20° C. to about 40° C. which is more typical of conditions for LPG production, storage, and handling systems. The hydrocarbon product obtained from the practice of the present invention will preferably contain less than about 0.001 wt % of fluoroalkanes and a negligible amount of hydrofluoric acid, preferably after further treatment, such as being passed through a KOH bed or other suitable absorbent for the hydrofluoric acid produced in the process.

In accordance with another aspect, a hydrocarbon stream containing a broader range of fluoroalkane contaminants can be treated. A process is provided for removing fluoroalkanes from hydrocarbon streams comprised of $C_3$ to $C_{10}$ hydrocarbons and containing from about 0.01 to about 3 wt. % $C_3$ to $C_5$ fluoroalkanes, wherein the process comprises contacting the fluoroalkane-containing hydrocarbon stream with an adsorbent having strong acid functionality, which contacting is performed at a temperature from about −40° C. to about 60° C. In one embodiment, the fluoroalkane-containing hydrocarbon stream includes from about 1 to about 3 wt. % $C_3$ to $C_5$ fluoroalkanes. For example, and as embodied herein, the adsorbent can be housed in at least two reactors, and the fluoroalkane-containing hydrocarbon stream is introduced to the at least two reactors in series. The adsorbent can be any one of the absorbents described herein.

Additionally, or alternatively, and in accordance with another aspect of the subject matter described herein, a conditioning process is provided for a strong acid adsorbent of the present application to increase the activity of the adsorbent in removing the fluoroalkane impurities from a hydrocarbon feed stream. As disclosed herein, a process is provided, including providing an adsorbent for conditioning, optionally, applying water to the adsorbent, applying an alcohol to the adsorbent, and drying the adsorbent at an elevated temperature. In one embodiment, the catalyst is a strong acid adsorbent, such as any one of the adsorbents described herein. The alcohol can be an isopropyl alcohol. The adsorbent can be dried at a temperature of from about 20° C. to about 80° C. (e.g., 60° C.). The conditioned catalyst can be provided for use in a process for removing fluoroalkanes from hydrocarbon streams, as described herein.

It has been found that washing the adsorbent with water for less than 1 minute, followed by washing with an alcohol (e.g., isopropyl alcohol), and then drying at an elevated temperature (e.g., at 60° C.) increases the ability of the catalyst to remove the fluoroalkane. Several alcohol washes, preferably 3 times, are performed to ensure complete removal of the water. The contact time and temperatures should be well below those which would induce the deterioration of the hydrocarbon feed and/or the adsorbent. The catalyst is dried for about 1 hour.

Alternatively, it is contemplated that the adsorbent could be washed initially with an alcohol without a water washing step. It is also contemplated that the washing steps can be repeated one or more times followed by drying. It is also contemplated that regeneration can be performed by washing the resin catalyst using 0.5-5% $H_2SO_4$ or 4-10% HCl for about 0.5 hour, followed by drying.

For purpose of illustration, and not limitation, an exemplary fluoroalkane removal system (1000) is depicted in FIG. 1.

As shown in FIG. 1, a fluoroalkane-containing feed (10) is provided. The feed stream can contain a mass flow controller (20), in addition to pressure gauges and controller (30). A thermocouple (40) is also provided. For compatibility with HF, Monel lines are used throughout the system.

The feed is directed to a defluorination reactor (50), where the feed stream is contacted with an adsorbent having strong acid functionality (e.g. sulfonic acid functionality). Examples of adsorbents having strong acid functionality, include, but are not limited to, Amberlyst® 15 and Purolite® D5174 and CT269 ion exchange resins. Preferably the adsorbent has a strong acid functionality is conditioned according to the conditioning process described above. After leaving the reactor, the process stream is introduced to a second thermocouple (60) for temperature control. A rupture disk (70) is also provided to protect the system from excessive pressure build-up. HF in the stream leaving the defluorination reactor is converted to KF and water in a KOH bed (80). The feed exiting the KOH bed is introduced to a $KF/H_2O$ Knockout pot (90) to provide a defluorinated hydrocarbon product stream (100) and a $KF/H_2O$ stream (110). Since the hydrocarbon product is lighter in density than the $KF/H_2O$ product, the hydrocarbon product stays on top and it is withdrawn as an overhead product stream (100).

Alternatively, the adsorbents can be housed in two or more reactors (e.g., at least two fixed bed reactors) in which the fluoroalkane-containing hydrocarbon feed is introduced to the at least two reactors in parallel to provide additional capacity, or in series to remove additional fluoroalkanes. In one non-limiting embodiment, two fixed bed reactors containing adsorbents are employed in series, with the second bed used to remove fluoralkane concentrations to below 1 ppm.

Figure 2:
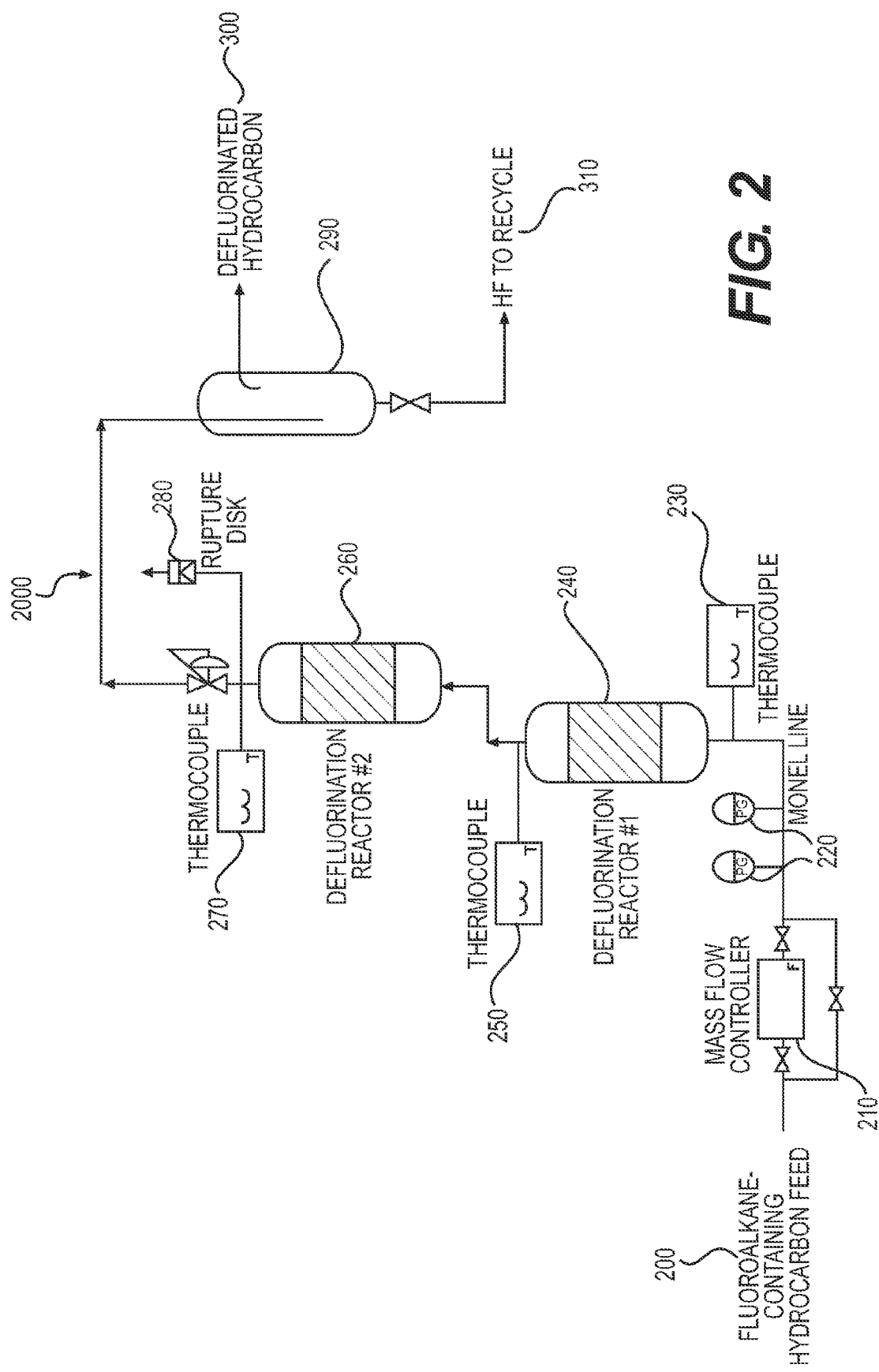
FIG. 2 is a schematic representation of an alternative fluoroalkane removal system suitable for fluoroalkane-containing hydrocarbon feeds containing high fluoroalkane concentrations in accordance with the process disclosed herein.

FIG. 2 depicts, for purposes of illustration and not limitation, an exemplary fluoroalkane removal system (2000) particularly applicable to fluoroalkane-containing hydrocarbon feeds containing high fluoroalkane concentrations (e.g., fluoroalkane feed concentrations of ≥1 wt %, based on the total weight of the fluoroalkane-containing hydrocarbon feed). A fluoroalkane-containing hydrocarbon feed (200) is provided. The feed is introduced to a mass flow controller (210) and pressure gauges and controllers (220). A thermocouple (230) is also provided to provide temperature control. The feed is introduced to two defluorination reactors (240, 260) in series. Additional thermocouples (250, 270) are provided downstream from the first and second reactors. A rupture disk (280) is also provided after the second defluorination reactor to protect the system from excessive pressure build-up. The feed leaving the second defluorination reactor is introduced to a $KF/H_2O$ Knockout Pot (290) to provide a defluorinated hydrocarbon product stream (300) and a HF stream (310). The HF stream can be recycled to the HF alkylation reactor for re-use.

EXAMPLES

The present invention is illustrated in greater detail by the specific examples presented below. It is understood that these examples are illustrative embodiments and are not intended to be limiting in any way.

Example 1

Pyridinium Polyhydrogen Fluoride

A 250 mL polyolefin bottle was equipped with a polyolefin gas-inlet and drying tube inserted through the holes in the cap and sealed with Teflon tape. The bottle was charged with 37.5 g (0.475 mole) of pyridine and cooled in an acetone-dry ice bath. After the pyridine solidified, 87.5 g (4.37 mole) of anhydrous hydrogen fluoride was condensed from a cylinder into the bottle through the inlet tube. The amount of hydrogen fluoride was determined by weighing the bottle. After the hydrogen fluoride has cooled, the bottle was cautiously swirled with cooling until the solid dissolved. The solution was then safely allowed to warm to room temperature.

Tert-Butyl Fluoride

A 500 mL polyolefin bottle was equipped with a Teflon-coated magnetic stirring bar and a polyolefin drying tube inserted through a hole in the cap and sealed with Teflon tape. The bottle was charged with 4.88 g (0.066 mole) of tert-butanol and 100 mL of pyridinium polyhydrogen fluoride. The solution was allowed to stir for 5 hours at 0° C., after which 250 mL of petroleum ether was added, and stirring continued at 0° C. for another 15 minutes. A two-phase system resulted and was transferred to a 500 mL polyolefin reparatory funnel, and the bottom layer was discarded. One of the phases was an organic layer that was washed successively with 100 mL of water, 100 mL of saturated sodium hydrogen carbonate solution and again with 100 mL water, then dried over anhydrous magnesium sulfate. The temperature was maintained at about 0° C. The organic layer was filtered, and the tert-butyl fluoride was allowed to distill, yielding 2.8 g (55%) of a clear liquid boiling at 12° C.

Preparation of the Tert-Butyl Fluoride/n-Pentane Stock Solution 500 mL of cold n-pentane kept at 0° C. was poured in a glass graduated cylinder. To the n-pentane was added 2.3 mL of tert-butyl fluoride also kept at 0° C. The resulting solution was thoroughly mixed and analyzed by CAP-GC by the CGSB method for gasoline. The concentration of the tert-butyl fluoride was found to be 0.43 wt %. The solution was kept in the refrigerator at 0° C.

Example 2

This example describes the various adsorbents tested in the following examples:

Activated Alumina, 28×48 mesh, provided by the BASF Company, The Woodlands, Tex. under the product designation DD-6.

Activated Alumina, 28×48 mesh, provided by the BASF Company, The Woodlands, Tex. under the product designation CPN.

Activated Alumina, 7×14 mesh, provided by the BASF Company, The Woodlands, Tex. under the product designation HF-200.

Activated Alumina, 7×14 mesh, provided by the BASF Company, The Woodlands, Tex. under the designation HF-200 XP.

Davisil® Silica gel, Grade 646 obtained from Grace Davison.

Amberlyst® 15 ion exchange resin obtained from Sigma-Aldrich, Cat. #216380-25G.

Dynasorb® 200 Attapalgite Clay, 24×48 mesh obtained from Dynamic Catalysts and Adsorbents Inc.

Spent MHIS catalyst characterized by the following elemental composition: 38.3 wt % Al, 0.5 wt % Si, 6.8 wt % Co, 29.9 wt % Mo, 19.3 wt % O, and 5.7 wt % S.

Spent RT-601 catalyst (hydrotreating catalyst) characterized by the following elemental composition: 6.1 wt % C, 1.4 wt % H, 8.2 wt % O, 36.1 wt % Al, 2.1 wt % Si, 9.3 wt % S, 6.0 wt % Co and 30.8 wt % Mo.

Spent FCC (fluid catalytic cracking) alumino-silicate catalyst characterized by the following elemental composition: 41.7 wt % Al, 32.3 wt % Si, 5.7 wt % 5 and 20.3 wt % O.

Spent MHIS D-116B catalyst characterized by the following elemental composition: 7.0 wt % C, 1.5 wt % H, 8.1 wt % O, 38.8 wt % Al, 1.5 wt % Si, 7.5 wt % S, 7.7 wt % Ni and 27.9 wt % Mo.

Preparation of the Sulfonated Silica Gel

The sulfonated silica gel adsorbent was prepared by stirring at ambient temperature (25° C.) 150 g Davisil® grade 646 silica gel with 400 mL chloroform and 50 mL chlorosulfonic acid. The slurry was filtered, dried with a stream of nitrogen, and used without further treatment.

Preparation of the Attapalgite Clay Treated with Ammonium Sulfate

The sulfur loaded Attapalgite Clay was prepared by stirring at ambient temperature in a 250 mL glass beaker 20 g of Dynasorb® Attapalgite Clay with 1.3 g ammonium sulfate dissolved in 100 mL distilled water. The slurry was then filtered and dried at 100° C. for 3 hours.

Example 3

This example illustrates the effectiveness of sulfonated silica gel of this invention for removing tert-butyl fluoride at ambient temperature conditions. A 10% potassium hydroxide solution in methanol was ineffective for removing the tert-butyl fluoride. The process utilizing an untreated silica gel resulted in a modest removal of 21.7% of the tert-butyl fluoride whereas the process of the present invention utilizing a sulfonated silica gel gave an outstanding 100% removal of the tert-butyl fluoride present in the hydrocarbon sample.

Procedure 20 mL of stock solution C was placed in a 50 L crimped glass GC bottle with the material to be tested. The bottle was placed on a Lab-Line® Orbit Shaker and shook for 20 hours at 30° C. After that period, the n-pentane portion was analyzed by CAP-GC. The tert-butyl fluoride retention time was 9.97 minutes.

The results of the various tests are shown in Table 1.

TABLE 1

| Test # | Description | TBF, wt % 20 hours | % Removal |
|---|---|---|---|
| 1 | Stock TBF in n-pentane (0.43 wt %) Blank | 0.432 | 0 |
| 2 | 5 mL Aqueous KOH 10 wt % | 0.434 | 0 |
| 3 | 10 mL Methanolic KOH 10 wt % | 0.419 | 2.9 |
| 4 | 10 mL Methanolic KOH 10% with 10 wt % $H_2O$ | 0.418 | 3.1 |
| 5 | 0.10 g HF-200 | 0.414 | 4.0 |
| 6 | 0.10 g DD-6 | 0.420 | 2.7 |
| 7 | 0.10 g HF-200XP | 0.433 | 0 |
| 8 | 0.10 g CPN | 0.424 | 1.7 |
| 9 | 0.30 g HP-200 | 0.414 | 4.0 |
| 10 | 0.30 g Spent MHIS regen. Catalyst | 0.397 | 8.0 |
| 11 | 0.30 g Silica Gel | 0.338 | 21.7 |
| 12 | 0.30 g Attapalgite Clay/$(NH_4)SO_4$ | 0.421 | 2.5 |
| 13 | 0.30 g Spent RT-601 Catalyst | 0.383 | 11.2 |
| 14 | 0.30 g Spent FCC Catalyst | 0.344 | 20.3 |
| 15 | 0.30 g MHIS D-116B Catalyst | 0.416 | 3.6 |
| 16 | 0.30 g sulfonated Silica Gel | 0 | 100 |
| 17 | 0.10 g sulfonated Silica Gel | 0 | 100 |
| 18 | 0.30 g Amberlyst ® 15 ion exchange resin | 0.010 | 97.8 |
| 19 | 0.10 g Amberlyst ® 15 ion exchange resin | 0.010 | 97.8 |

Example 4

Preparation of Tert-Butyl Fluoride

The tert-butyl fluoride used in this Example prepared by FluoroTech, LLC (Gainesville, Fla., USA) using the following procedure.

$$(CH_3)_3C-OH + (CH_3)_2N-SF_3 \xrightarrow[\text{diglyme}]{-50° C. \text{ to RT}} (CH_3)_3C-F \quad \text{Equation (2)}$$

methyl-DAST      bp 12° C.

t-butanol (5.0 g, 0.068 mol) was dissolved in diglyme (30 mL) in a 100 mL three-necked flask connected to an acetone-dry ice trap, and the mixture was cooled to −50° C. (Dimethylamino)sulfur-trifluoride (methyl-DAST) (9.0 g, 6.6 mL, 0.0676 mol) in diglyme (20 mL) was added dropwise in 2 h. The reaction mixture was kept stirring at this temperature for 0.5 h, then warmed to room temperature and stirred overnight. The product was then distilled at reduced pressure (50 mmHg), the temperature of the bath being kept below 25° C. to avoid distilling any remaining starting material. The obtained t-butyl fluoride product was colorless liquid 4.3 g (84%), purity: >96%. The product was be further purified by redistilling over a small amount of potassium fluoride to obtain a purity of >98%. 1H NMR, δ 1.38 (3JFH=21 Hz); 19F NMR, δ−131.2 (10 peak multiplet, 3JHF=21 Hz); 13C NMR, δ 94.1 (d, 1JFC=162 Hz), 28.7 (d, 2JFC=25 Hz).

Preparation of the Tert-Butyl Fluoride-n-Pentane Stock Solution

Approximately 220 mL of cold n-pentane kept at 0° C. was poured in a glass graduated cylinder. To the n-pentane was added approximately 1.7 mL of tert-butyl fluoride which was also kept at 0° C. The solution was mixed thoroughly and analyzed by CAP-GC using the CGSB (Canadian General Standards Board, 3.0 14.3-99) method for gasoline. The concentration of tert-butyl fluoride was 0.615 vol %. The solution was kept in the refrigerator at 0° C. Lower concentrations of the tert-butyl fluoride-n-pentane stock solution was obtained by diluting with pentane. To obtain 0.45 vol % of tert-butyl fluoride, 60.5 mL of n-pentane was added to 159.5 mL of the stock solution.

n-Butane Contaminated with Fluoroalkane

Contaminated n-butane was sampled directly from the alkylation unit in a refinery. The fluoroalkane-containing n-butane was sampled into a 43-lb forklift cylinder. The sampled fluoroalkane-containing hydrocarbon feed was found to contain 1374 ppm of fluoroalkane, 19.6 mol % iC4, 70.2 mol % nC4, 9.4 mol % iC5, and 0.6 mol % C6+.

The catalyst resins list below were tested:
Amberlyst® 15 resin obtained from Sigma-Aldrich, Cat. #216380-500G;
Amberlyst® 15WET resin obtained from Rohm & Haas;
Purolite® CT269DR catalyst resin obtained from Purolite.
Purolite® CT275DR catalyst resin obtained from Purolite.
Purolite® CT275 resin obtained from Purolite.
Purolite® CT252 resin obtained from Purolite.
Purolite® D5174DR resin obtained from Purolite.

Conditioning of the Strong Acid Catalyst Resin

The catalyst resin was conditioned using the following procedure.

Approximately 30 g of the resin was added to 250 mL of deionized water in a beaker and swirled for 1 minute. The wet resin was poured into a 38-micron sieve to separate the resin from the water. Approximately 250 mL of isopropyl alcohol (IPA) was pour slowly over the resin in the sieve to displace all the water. The IPA wash was repeated twice. The resin was dried with $N_2$ under the fumehood until the color of the resin changed to light brown. The resin was then dried in an oven at 60° C. for 1 hour. The dried resin was stored in a dessicator.

The conditioned strong-acid catalyst resin as disclosed herein was very effective in removing the tert-butyl fluoride at ambient temperature conditions. The wet catalyst resin was ineffective in removing the tert-butyl fluoride. The dry form of the catalyst resin when used as is, moderately removed the tert-butyl fluoride. The conditioned catalyst resin gave the highest removal of the tert-butyl fluoride. For example, the wet form of CT275 only removed 5% of the tert-butyl fluoride when 20 mL of pentane containing 0.45 vol % of tert-butyl fluoride was treated with 0.3 g of the CT275. The dry form of the CT275DR, which contains a maximum of 3% moisture, removed 77 vol % of tert-butyl fluoride when 10 mL of pentane containing 0.37 vol % of tert-butyl fluoride was treated with 0.15 g of the dry CT275DR. The conditioned wet CT275 and the conditioned dry CT275DR removed 92 vol % and 95 vol % of tert-butyl fluoride, respectively.

Testing Procedure 20 mL of stock solution A containing 0.4-0.45 wt % tert-butyl fluoride in pentane was placed in a 50 mL crimped glass GC bottle with the material to be tested. The bottle was placed on a Lab-Line® Orbit Shaker and shaked for 20 hours at 30° C. After that period, the n-pentane portion was analyzed by CAP-GC. The tert-butyl fluoride retention time was 10.8 minutes.

In another set of tests, 10 mL of stock solution B containing 0.35-0.37 wt % tert-butyl fluoride in pentane was placed in a 50 mL crimped glass GC bottle with the material to be tested. The bottle was placed on a Lab-Line® Orbit Shaker and shaked for 20 hours at 30° C. After that period, the n-pentane portion was analyzed by CAP-GC. The tert-butyl fluoride retention time was 10.8 minutes.

In still another set of tests, 20 mL of stock solution C containing 0.3-0.35 wt % tert-butyl fluoride in pentane was placed in a 50 mL crimped glass GC bottle with the material to be tested. The bottle was placed on a Lab-Line® Orbit Shaker and shaked for 20 hours at 30° C. After that period, the n-pentane portion was analyzed by CAP-GC. The tert-butyl fluoride retention time was 10.8 minutes.

The following results were obtained. Tests 1-7 were performed using the procedure in paragraph 0063; tests 8-11 were performed using the procedure in paragraph 0064; and tests 12-20 were performed using the procedure in paragraph 0065.

| Test # | Description | Pentane Vol (mL) | Catalyst Wt (g) | Vol % TBF, Initial | Vol % TBF, Final | Conversion, vol % |
|---|---|---|---|---|---|---|
| 1 | CT252 (wet) | 20 | 0.101 | 0.450 | 0.433 | 3.8 |
| 2 | CT252 (wet) | 20 | 0.204 | 0.450 | 0.426 | 5.3 |
| 3 | CT252 (wet) | 20 | 0.298 | 0.450 | 0.433 | 3.8 |
| 4 | CT252 (wet, no TBF) | 20 | 0.322 | 0 | 0 | 0.0 |
| 5 | CT275 (wet) | 20 | 0.102 | 0.450 | 0.429 | 4.7 |
| 6 | CT275 (wet) | 20 | 0.196 | 0.450 | 0.426 | 5.3 |
| 7 | CT275 (wet) | 20 | 0.301 | 0.450 | 0.428 | 4.9 |
| 8 | Purolite D5174DR as is | 10 | 0.153 | 0.366 | 0.053 | 85.5 |
| 9 | CT275DR as is | 10 | 0.146 | 0.366 | 0.086 | 76.5 |
| 10 | CT275(Wet) conditioned | 10 | 0.157 | 0.366 | 0.029 | 92.1 |
| 11 | Amberlyst 15 Wet | 10 | 0.149 | 0.366 | 0.344 | 6.0 |
| 12 | Amberlyst 15 as is | 20 | 0.292 | 0.348 | 0.075 | 78.4 |
| 13 | CT275DR conditioned | 20 | 0.304 | 0.348 | 0.016 | 95.4 |
| 14 | CT269DR conditioned | 20 | 0.306 | 0.348 | 0.012 | 96.5 |
| 15 | Amberlyst 15 conditioned | 20 | 0.304 | 0.348 | 0.009 | 97.4 |
| 16 | D5174DR conditioned | 20 | 0.294 | 0.348 | 0.009 | 97.4 |

-continued

| Test # | Description | Pentane Vol (mL) | Catalyst Wt (g) | Vol % TBF, Initial | Vol % TBF, Final | Conversion, vol % |
|---|---|---|---|---|---|---|
| 16 | CT269DR conditioned | 20 | 0.113 | 0.348 | 0.034 | 90.2 |
| 18 | Amberlyst 15 conditioned | 20 | 0.101 | 0.348 | 0.033 | 90.5 |
| 19 | CT275DR conditioned | 20 | 0.097 | 0.348 | 0.045 | 87.1 |
| 20 | D5174DR conditioned | 20 | 0.099 | 0.348 | 0.022 | 93.7 |

"Wet" catalyst indicates moisture content of 50-60%, and it has not been washed with alcohol.

What is claimed is:

1. A process for conditioning an adsorbent comprising:
   (a) providing an adsorbent having strong acid functionality tier conditioning;
   (b) applying water to the adsorbent;
   (c) applying an alcohol to the adsorbent;
   (d) repeating act (c) at least an additional two times; and
   (e) drying the adsorbent at an elevated temperature, wherein the adsorbent is dried at a temperature of from about 20° C. to about 80° C.

2. The process of claim 1, wherein the acid functionality of the adsorbent is sulfonic acid.

3. The process of claim 1, wherein the adsorbent is selected from the group consisting of mineral based adsorbents and organic based adsorbents.

4. The process of claim 1, wherein the adsorbent is a mineral based adsorbent selected from the group consisting of zeolites, clays, and silica gels.

5. The process of claim 1, wherein the adsorbent is comprised of a silica gel with a sulfonic acid functionality.

6. The process of claim 1, wherein the adsorbent is comprised of a polymeric strong cation exchange resin.

7. The process of claim 6, wherein the polymeric strong cation exchange resin is a styrene/divinyl benzene copolymer resin having a sulfonic acid functionality.

8. The process of claim 1, wherein water is applied to the adsorbent prior to the application of the alcohol.

9. The process of claim 8, wherein the alcohol is isopropyl alcohol, methanol, ethanol, n-propanol, n-butanol, isobutanol, sec-butanol, or tert-butanol.

10. The process of claim 1, wherein the adsorbent is dried at a temperature of about 60° C.

* * * * *